United States Patent [19]

Gonser

[11] 4,229,658

[45] * Oct. 21, 1980

[54] XENON LIGHT APPARATUS FOR SUPPLYING ULTRAVIOLET AND VISIBLE SPECTRA

[75] Inventor: Donald I. Gonser, York, Pa.

[73] Assignee: Dentsply Research & Development Corp., Milford, Del.

[*] Notice: The portion of the term of this patent subsequent to Sep. 5, 1995, has been disclaimed.

[21] Appl. No.: 934,912

[22] Filed: Aug. 18, 1978

Related U.S. Application Data

[63] Continuation-in-part of Ser. No. 806,316, Jun. 13, 1977, Pat. No. 4,112,335, which is a continuation of Ser. No. 560,290, Mar. 20, 1975, abandoned.

[51] Int. Cl.$^2$ ................................................ G01J 1/00
[52] U.S. Cl. ............................... 250/504 H; 313/184; 315/326; 250/493
[58] Field of Search .................... 313/184, 198, 224; 315/241 R, 326, 336; 250/493, 504

[56] References Cited

U.S. PATENT DOCUMENTS

| | | | |
|---|---|---|---|
| 2,261,215 | 11/1941 | Bird | 250/504 |
| 2,977,508 | 3/1961 | Germeshausen | 313/196 X |
| 3,218,510 | 11/1965 | Schulz | 313/197 X |
| 3,350,602 | 10/1967 | Germeshausen et al. | 313/196 X |
| 3,712,984 | 1/1973 | Lienhard | 250/504 |
| 3,868,513 | 2/1975 | Gonser | 250/504 |
| 3,970,856 | 7/1976 | Mahaffey et al. | 250/493 |
| 4,149,086 | 4/1979 | Nath | 250/504 |

Primary Examiner—Eugene R. La Roche
Attorney, Agent, or Firm—Woodcock, Washburn, Kurtz, Mackiewicz & Norris

[57] ABSTRACT

A handheld lamp is disclosed wherein the light source is a rapid pulse unconfined xenon arc tube containing more than three atmospheres of xenon gas pressure, and providing a selectable spectral output of ultraviolet, visible, or ultraviolet and visible wavelengths. The lamp contains a radiation guide for directing the generating light, the tip of which is maintained cool for effective use such as in curing tooth restorative materials. The lamp may be located in the power supply and light delivered through a flexible light pipe.

22 Claims, 4 Drawing Figures

U.S. Patent  Oct. 21, 1980  Sheet 1 of 2  4,229,658
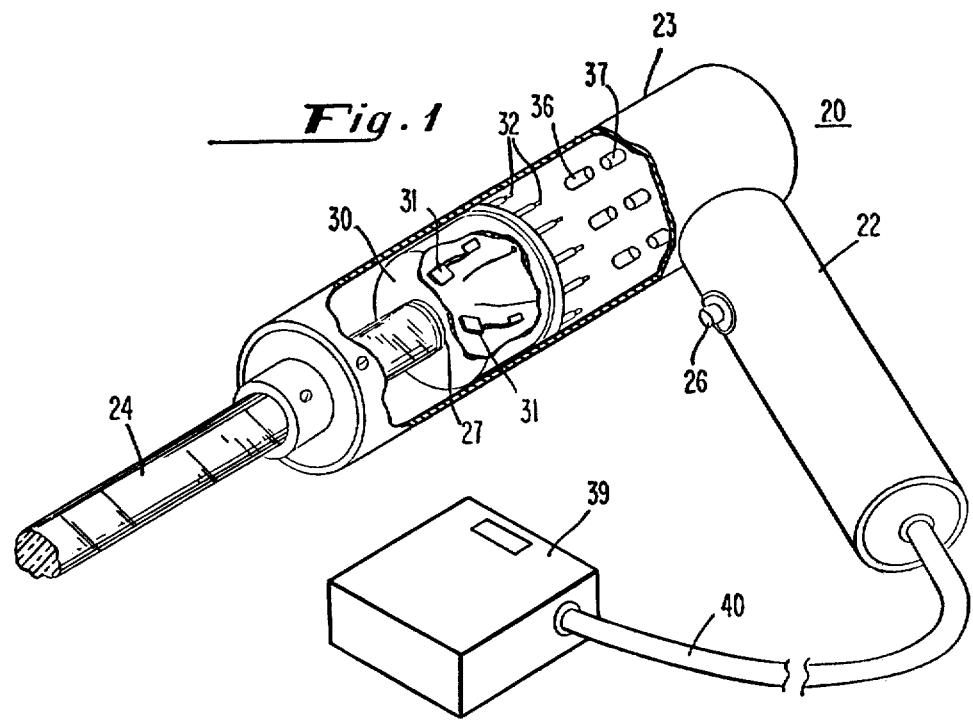
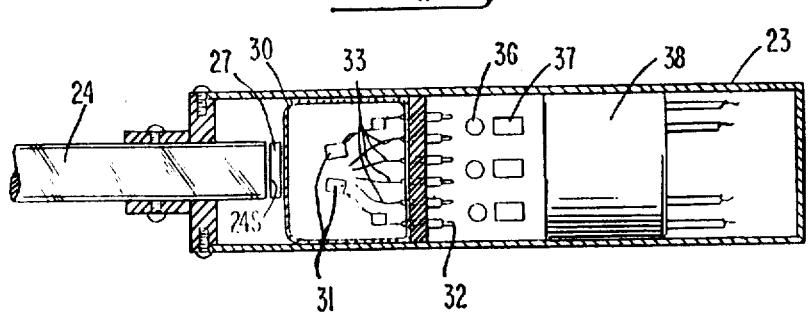

XENON LIGHT APPARATUS FOR SUPPLYING ULTRAVIOLET AND VISIBLE SPECTRA

REFERENCE TO RELATED APPLICATION

This application is a continuation-in-part of pending application Ser. No. 806,316, filed June 13, 1977, U.S. Pat. No. 4,112,335, which prior application is a continuation of application Ser. No. 560,290, filed Mar. 20, 1975, abandoned. Any portions of such parent applications not included herein are incorporated by reference.

BACKGROUND OF THE INVENTION

This invention adds to the field of pulsed discharge light sources and, more particularly, pulsed light sources which are efficient in delivering light energy in the ultra-violet and/or visible range of the electromagnetic spectrum and are capable of being adapted to deliver such spectra of light energy to a small area.

DESCRIPTION OF THE PRIOR ART

In the fields of medicine and dentistry there have been recent developments which have increased the interest in and use of light energy in the ultraviolet and visible ranges both as a treatment agent as well as for its ability to be used to activate the polymerization of certain kinds of polymeric compositions to produce splints, dental sealants, dental filling materials and dental adhesives for orthodontic appliances and the like. In particular, in the protection of the teeth of human beings, and especially children, an important development in decreasing the incidence of cavities involves the technique of applying a liquid resin which penetrates crevices in the occlusal or biting surfaces of teeth, and which can be polymerized to form a tough adherent coating. Ultraviolet radiation has been used extensively as one mechanism for activating that resin polymerization. Other applications for ultraviolet activation of resin polymerization are for tooth filling materials for tooth restoration, cements for orthodontic attachments and polymerization techniques for crown and bridge prosthesis.

Ultraviolet lamps currently available for providing ultraviolet light radiation for the activation and curing of polymerizable liquid coatings or sealants and the like have generally been most suitable for techniques not requiring great penetration of the polymerizable mass of material. To be suitable for such applications an ultraviolet light would have to be sufficiently rich in those wavelengths which are most efficient for the curing of the polymer in question. Otherwise, it would be subject to the disadvantage of having to be hand-held for too long a period of time thereby inducing both patient and operator discomfort. Likewise, ultraviolet light devices previously available in the art might be prone to building up an uncomfortable amount of heat, particularly where the source is located in the handpiece, if they were required to cure material to a sufficient depth that the device was required to be on longer than a normally tolerable period of time.

The basic cause for any excessive heating which might occur in prior art devices derives from the fact that they were relatively insufficient in producing emissions at the desired ultraviolet wavelengths for the polymerization of the materials being used, i.e., approximately between 320 nanometers and 390 nanometers. In addition, the devices previously in use required a long warm-up time thereby tending to reach a high threshold temperature while not in use thereby diminishing the useful working life. Additionally, prior art devices have been characterized by undesirably high total ultraviolet light output flux at a single wavelength or no more than a few wavelengths for a given spectral region.

It has now become desirable to provide a radiation source adapted for curing visible radiation activated monomeric dental materials, as well as ultraviolet activated materials. The visible range of wavelengths is approximately between 400 and 800 nanometers, but the range of primary interest is about 400 to about 500 nm. The visible light activated materials are cured efficiently by light in the 400 to 500 nm range, and in addition it is desirable to substantially attenuate those wavelengths above about 500 nm. The opearator of a light source with large amounts of radiated energy in the 500-700 nm wavelength range is subject to eye fatigue and after image. However, by passing a low level output in the 500 to 700 nm wavelength range, the operator can see a slight amount of light so as to be able to direct the radiation accurately on the intended target. Thus, whether or not the restorative material is cured by visible light, it is desirable to provide a low level light component in the medium and high visible range, i.e., between 500-700 nm.

For curing of materials which respond to visible light, it is desirable to have high output (approximately $>70$ mw/cm$^2$ at contact, 400 to 500 nm). It is to be noted that wavelengths in this low visible range can penetrate deeper into the restorative material than can the ultraviolet wavelengths. Additionally, the visible wavelengths can penetrate tooth structure, whereas the ultraviolet wavelengths are more greatly attenuated. Thus, there is a definite use for the low visible portion of the spectrum.

SUMMARY OF THE INVENTION

It is the primary object of this invention to provide a light source which is highly efficient in the desired wavelength ranges of ultraviolet and near visible emissions for the polymerization of tooth restorative and sealant materials so as to cause rapid curing of such materials with a lower total power output.

It is a further object of this invention to provide a device characterized by providing efficient emission of ultraviolet and/or low visible light which is projected through a light transmitting and focusing means for delivery of the light to a small area in a restricted location.

It is another object of this invention to provide a light source which is capable of being handheld, which delivers an optimum amount of power at wavelengths greater than about 320 nanometers, and which is in combination with a radiation guide to further attenuate unwanted wavelengths.

It is a further object of this invention to provide a device for selectively delivering ultraviolet radiation and/or low visible light, which device is characterized by having high efficiency emission in near ultraviolet and low visible wavelength ranges, and which provides a minimum amount of generated heat due to an increased operating efficiency and the elimination of emissions at unwanted wavelengths.

It is another object of this invention to provide a small handpiece efficient for providing near ultraviolet and/or low visible wavelength energy, which handpiece is operable with very low heat and minimal visible radiation in the 500-700 nm range.

In accordance with the above objectives, there is provided by the present invention a light source device, having a lightweight structure suitable for handheld operation, and having an unconfined arc xenon tube light source in operative association with light delivery means for delivering ultraviolet radiation and/or low visible light to a restricted location, the device having circuitry for pulsing the light source at preselected voltages and currents so as to produce a rich source of near ultraviolet radiation and a desired level of low visible light. The tube is operated at above 3 atmospheres pressure, optimally at about 4 atmospheres, and the irradiated energy is limited to wavelengths greater than 300–320 nanometers. Optical filters are mounted in the optical path to limit the wavelength range to about 300–400 (UV only), 400–500 (low visible only), or 300–500 (UV and low visible). The handpiece is equipped with a radiation guide which provides further attenuation of unwanted wavelengths. In an alternate embodiment, the light source is housed with the power supply separate from the handpiece, and the light radiation is connected to the handpiece by flexible light fibers or another type of flexible light conducting liquid filled tubing.

BRIEF DESCRIPTION OF THE DRAWINGS

FIG. 1 is a perspective view of a handheld light source in combination with a power supply and pulse timing circuitry which is connected to the handheld device through a connector.

FIG. 2 is a cross-sectional view of the portion 23 of the handheld light source, showing the relationship of the light source to the light pipe which delivers the ultraviolet radiation.

DESCRIPTION OF THE PREFERRED EMBODIMENTS

Figure 3:
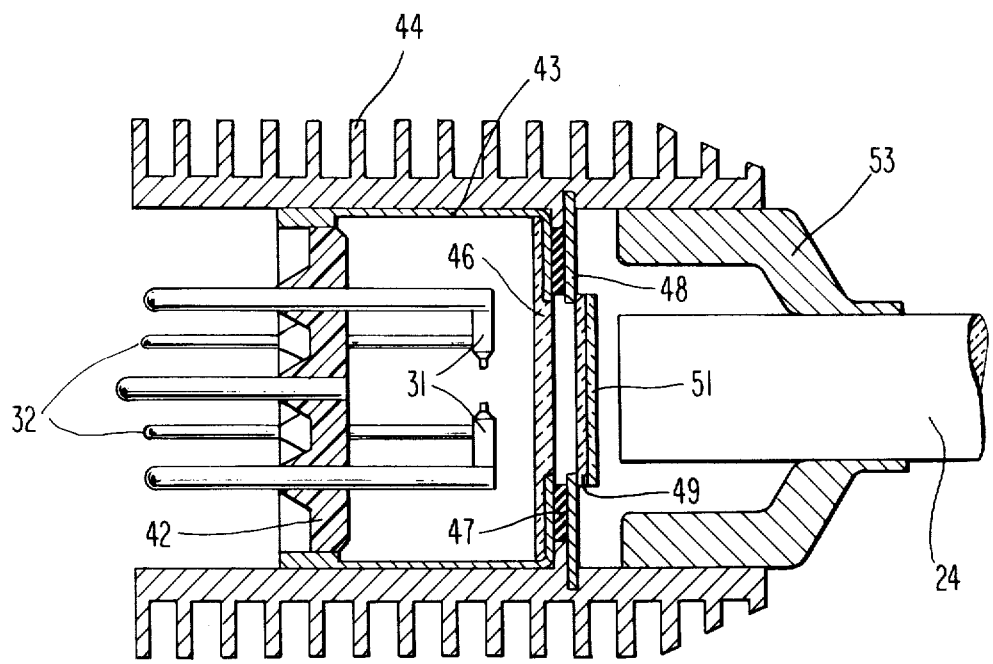
FIG. 3 is an exploded diagrammatic view of a portion of the handheld apparatus, illustrating the arrangement of optical filters for obtaining the desired spectral range.

Referring now to FIG. 1, the handpiece apparatus of this invention is illustrated in perspective view in combination with a separate power source. A handheld device 20, in the form of a gun, is comprised of handle 22 and the light source housing 23. Handle 22 contains a suitable located button 26 which operates an electrical switch, not shown, to trigger a discharge of electrical energy so as to pulse the light source.

A light generating tube 30, cylindrical in geometry, is contained within the inner cylindrical surface of metallic housing portion 23, as seen in FIG. 1 and FIG. 2. Light generating tube 30 is an unconfined xenon arc flash tube, the xenon gas pressure being maintained at a high pressure, i.e., greater than 1 atmosphere. By unconfined, it is meant that the xenon arc is not confined by a glass envelope, but rather is freely formed between the electrodes, such as the configuration of sub-atmospheric tubes manufactured by EG & G of Salem, Massachusetts. The typical lamp tube employs a number of trigger electrodes 33 (FIG. 2) for the purpose of initiating the main arc for each pulsed flash of light, which trigger electrodes help to stabilize and trigger the main arc and to maintain the xenon arcs with respect to position and continuity. The unconfined arc flash tube of the present invention contains a pair of closely spaced electrodes 31, anode and cathode respectively, between which the main arcs form. An unconfined arc flash tube of this configuration permits an arc than can be as small as ⅛ inch, (or even smaller) which is an excellent arc plasma size for directing a high percentage of the total produced light to the light rod 24 or light pipe 203 without the requirement of special reflectors and focusing devices. The envelope of tube 30 is suitably made of metal with a glass window such as CORNING 0080, which cuts off unwanted light emissions at wavelengths below 300–320 nanometers.

Typically, the superatmospheric unconfined arc flash tube as disclosed in this invention has the following spectral efficiency for wavelengths above 320 nm:

| WAVELENGTH | % EMISSION |
|---|---|
| 320 nm–500 nm | 38.5% |
| 500 nm–700 nm | 26.9% |
| 700 nm–900 nm | 20.0% |
| 900 nm–11,000 nm | 14.6% |
| 320 nm–11,000 nm | 100.0% |

By contrast, the typical subatmospheric confined arc flash tube has the following spectral efficiency:

| WAVELENGTH | % EMISSION |
|---|---|
| 320 nm–500 nm | 11.3% |
| 500 nm–700 nm | 12.8% |
| 700 nm–900 nm | 13.1% |
| 900 nm–1,000 nm | 14.7% |
| 1,100 nm–11,000 nm | 48.1% |
| 320 nm–11,000 nm | 100.0% |

From the above, it is seen that the unconfined arc tube of the present invention produces a much greater output in the desired range of 320 to 500 nm. Since the color temperatures for the superatmospheric unconfined arc tube are shifted toward the shorter wavelengths, much less tube heating is experienced (the most efficient heating wavelengths, infrared, being in the 900 nm–11,000 nm range). This low level of heating is, of course, a very desirable feature for the intended dental use of the device.

The preferred gas to be used in the unconfined arc tube of this invention is xenon. The xenon tube is characterized by having an arc color temperature in the area of 24,000° K. and provides a substantial output continuum through the spectral range of 300 nm to 500 nm. This is in contrast to the typical prior art light source which, for example, concentrates a high percentage of its output energy at peaks over the following wavelengths: 313, 334, 365, 404.5 and 435.8 nanometers. Other prior art sources, such as mercury vapor sources, are line sources and do not provide a continuum of energy throughout the useful spectral range. Tungston lamp sources provide a continuum over the desired wavelength range but are characterized as having an undesirably high output in the infrared which must in part be removed from the output with expensive heat absorbing and dichroiac filters. Typically these lamps have a very short life which must be operated at relatively high color temperatures to obtain high UV and low visible output (300 to 500 nanometers). Typically the color temperature must be about 3400° Kelvin and lamp life will range between 10 and 25 hours. Unconfined xenon arcs have a life of 260 hours, require no infrared filtering, and operate at a color temperature of 24,000° K. It is important, for the applications discussed in the background, that the light source provide an output which is substantially continuous throughout the desired range, i.e., not have a high percentage of its output concentrated in one or several narrow peaks but have it spread out reasonably uniformly throughout the range. The xenon tube of this invention provides just such characteristic, which permits more rapid curing with a smaller energy per wavelength in its output over the required spectrum. For example, using the source of this invention has enabled twice as efficient a cure as a prior art device, which increased efficiency is achieved with less total emitted energy.

In describing the preferred gas as xenon, it is to be noted the gas can have portions of other elements such as Krypton, argon, neon or helium mixtures. The desired characteristic of the gas is that it have the high color temperature and substantial output continuum as described above.

In tests, it has been demonstrated that as the xenon gas pressure in the tube is increased, the level of light output increases considerably for the same electrical energy input. For example, in using this tube for curing a sealant sample of a given thickness, a time period of 10 minutes at a flash repetition rate of 60 pps was required when the xenon gas pressure was equal to atmospheric pressure. Increasing the xenon gas pressure to 3 atmospheres, while using the same repetition rate and pulse length, enabled curing of the sample of same thickness in two minutes. Other investigations have shown that with further increased pressures, additional increased ultraviolet and low visible light curing efficiency is obtained. In practice, a pressure of 4 atmospheres has been found to be optimal. The range of 3 to 10 atmospheres is desirable for operation of the device of this invention.

Specific tests have been performed on the rapid pulsed xenon device of this invention to provide data illustrative of the unique optimization obtained by operation at a gas pressure of 3 atmospheres or more. In the tests, power input to the arc tube was held constant, and ultraviolet and low visible output variations were measured as a result of variations in xenon pressure only. In increasing the xenon pressure from 3 to 4 atmospheres, a large increase was seen in the power output within the 300–500 nm range by a factor of almost 2 times. Controlled xenon pressure increases above 4 atmospheres produced increases in output for the same range of approximately 10% per atmosphere. Thus, increasing the pressure above 3 atmospheres gives an unexpected result in terms of output in the desired wavelength range. Operation around 4 atmospheres is optimum, since the resulting relatively small increases in output at greater pressures are accompanied by instability of operation. Also, at higher pressures the safety margin of the tube envelope optical window against fracture is reduced to unacceptable levels. In summary, then, operation above 3 atmospheres provides uniquely advantageous operation for the device of this invention, where wavelengths below about 300 nm are cut off, and those between 300 and 500 nm are utilized. At just 3 atmospheres, the ultraviolet and low visible power available for dental purposes (e.g., curing restorative and sealant materials) is not sufficient; at 4 atmospheres, there is available all the power that is needed to perform the curing operations in the desired time.

Still referring to FIGS. 1 and 2, the light pipe 24 is mounted coaxially with light housing member 23, and in operative relationship with light generating source 30, such that the main arc between electrodes 31 are positioned right in front of the inner end surface 24S of light pipe 24. In this way, there is efficient collection of the emitted ultraviolet and low visible light input pipe 24. As seen in FIG. 4, pipe 24 has a curved end, and may be adapted with a focusing piece 25 for focusing the emitted light onto the desired tooth surface. A light filter assembly 27 may be placed between source 30 and pipe 24, as is discussed in greater detail in connection with FIG. 3. Pipe 24 is suitably a quartz rod.

Most of the pulse generating circuitry is contained in housing 39 (as seen in FIG. 1) which is connected through a coaxial transmission cable 40 to the gun device 20. As explained in detail in referenced application Ser. No. 806,316, the circuitry in housing 39 provides the flash discharge energy to the lamp 30. Additionally, pulse signals are connected to the tube socket terminals 32. The generated trigger pulses have a fast rise time of less than about two microseconds, providing the starting arc that initiates the main discharge arc. Accordingly, it is desirable to have a low inductance and low resistance connnection between the discharge circuitry and the tube discharged electrodes. This may be provided by use of the coaxial cable 40. It has been found that the difference between the use of an ordinary double lead connection and the coaxial lead is substantial, the coaxial lead providing a much lower circuit inductance. When the rise time of the high frequency pulses is allowed to increase due to transmission inductance, the resulting light energy output from the tube, when pulsed, is decreased significantly. Tests have shown that the percentage of the energy discharge through the tube during a flash, which is converted to light, is about three times as great when a coaxial line is utilized.

Figure 4:
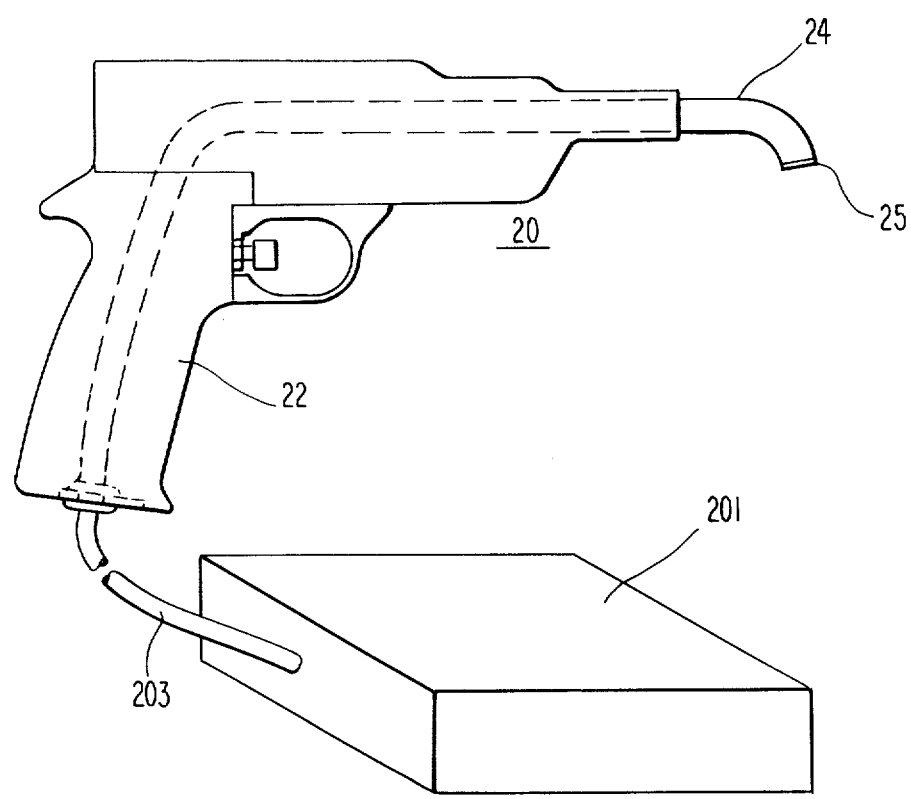
FIG. 4 is a schematic representation of a system using the light source apparatus of this invention and employing a light pipe between the source and the handpiece.

Referring now to FIG. 3, there is seen a schematic representation of an optical filter assembly for providing the desired spectral range of radiated wavelengths. In the embodiment of FIG. 3, the xenon tube light source is mounted within the handpiece, as illustrated in FIG. 1. Metallic tube case 43 of tube 30 is shown supporting a tube base 42, in which the tube pins 32 are mounted. Tube pins 32 are connected to electrodes 31. A metallic heat sink, or thermal radiator 44 is illustrated as being in thermal contact with tube casing 43. The end of tube case 43 defines an opening which is filled by glass optical window 46. This window is suitably made of Corning type 0080 optical glass which cuts off wavelengths below about 300 nm. Mounted to the outside of the case and window is acoustical isolated pad 47 suitably of silicone rubber. To the outside of isolated pad 47 is an aluminum washer 48. Mounted to the outside of washer 48 are two optical filters 49 and 51 which are held in place by a suitable filter mount, not shown. Two such filters are shown, although only one or the other may be used as desired. However, provision for two filters enables selecting the source to provide either the ultraviolet range, the low visible range, or a combination of ultraviolet and low visible. Mounted in close proximity to the two optical filters is the radiation guide 24, which is suitably a quartz cylinder of approximately 10 mm diameter. It is held in place by member 53 as shown.

To obtain a spectrum of ultraviolet radiation only, filter 49 may be a filter type UG-12, a bandpass filter passing about 300–400 nm, while filter 51 is a filter type UV-34 which is a sharp cutoff filter cutting off wavelengths below about 340 nm.

For passing visible radiation only, filter 49 is suitably a filter type L-42 which passes wavelengths above about 420 nm, while filter 51 is a type B-380, a bandpass filter passing about 300–480 nm.

To obtain a spectrum comprising both the ultraviolet and low visible, filter 49 may be the type B-380, while filter 51 is the type UV-34.

Alternatively, the ultraviolet spectrum alone can be obtained by using a combination of type WG-335 sharp cutoff filter which cuts off wavelengths below about 335 nm and type UG-12 ultraviolet bandpass filter.

For each of the above combinations, together with the cutoff characteristics of the Corning 0080 glass window, a very good bandpass characteristic for the desired range is obtained.

Still referring to FIG. 3, the radiation guide or rod 24 may be chosen according to the desired spectrum range. For providing just the low visible light, i.e., about 400–500 nm, guide 24 is preferably a bundle of optical glass fibers. Certain optical glass fibers in combination with the above described optical filters are efficient for attenuating wavelengths outside the visible range of 400–500 nm, such that the operator sees only the very soft blue projection of light, enabling proper aiming of the handpiece to the target area but without transmitting longer wavelengths which cause fatigue and after-image problems. For ultraviolet radiation only, guide 24 is either quartz, quartz fiber, or a liquid-filled tuned pipe, tuned to the middle of the ultraviolet range. For a desired range embracing both the ultraviolet and the low visible spectrum, a quartz rod, quartz fiber, or glass fiber is suitable.

Referring now to FIG. 4, there is shown a diagrammatic view of another embodiment of this invention. In this embodiment, the power supply and all of the electronic circuitry are housed in an external housing 201, along with the light source and filter assembly. Thus, in this embodiment, the light pulses are generated externally to the actual handheld device which delivers the curing light pulses to the tooth surface. Connecting between housing 201 and the handheld delivery means 20 is a light pipe, or light guide 203. Such light guides or light pipes are commercially available, and are generally of either the fiber-optic type or the liquid filled pipe type. In this arrangement, the handpiece 20 can be very small, and in fact pencil-like in size. There are no heat problems associated with the handpiece itself since it is acting as simply a conduit for the light which is generated at an external point. Of course, the output of the source within housing 201 is, in this embodiment, adjusted to take into account any attenuation of the light as it is transmitted through the pipe 203 to the handpiece. Attenuation of wavelengths outside of the desired range is useful in maintaining the tip 25 as cool as possible. The liquid filled light guides can be made to be wavelength or bandpass selective, so as to complement the chosen filter assembly. Appropriate changes in the power supply voltage and other circuit parameters are a matter of design choice, and within the state of the art. Reference is made to FIG. 6 of application Ser. No. 806,316, which is equivalent to FIG. 4 of this application. The invention herein claimed embraces the configuration of the referenced FIG. 4.

The UV and low visible light source apparatus as described possesses unique advantages over any prior art device for efficiently producing power in the range of 300 to 500 nm. As soon as the pressure of the xenon is raised from 3 atmospheres, a substantial increase is achieved in power delivered within such range; sincethe largest increase is observed up to and around 4 atmospheres, the optimum design of the apparatus of this invention calls for the pressure to be greater than 3 and up to around 4 atmospheres. However, increased power in the desired range is observed up to a pressure of 10 atmospheres. As stated previously, for the apparatus disclosed, operation at the higher pressures is likely to be less stable, and the disclosed glass window is in greater danger of fracture. However, a stronger window (having the same cutoff characteristic) may be utilized, and the device may be usefully employed at the higher pressures for applications where greater power in any one of the 300–400, 400–500, or 300–500 nm ranges is necessary.

In addition to the above-described embodiments, the invention may embody a flexible plastic light fiber light pipe as guide 24, for delivery to the target. Plastic flexible fibers have characteristics, including relatively low cost, which make them attractive for this application. Also, it is to be noted that the filter assembly may be positioned at the output end of the light pipe. Placement of the filter or filters at the output end presents a reduced optical loss over the wavelengths of interest, i.e., 300 to 500 nanometers. In the handpiece configuration of FIG. 4, the filter 60 is suitably placed just before tip 25. Filter 60 consists of a disk about 6 mm in diameter and about 1.0 mm thick.

I claim:

1. Light source apparatus for delivering a substantial continuum of radiation within a range of about 300 to 500 nanometers to a restricted surface area, comprising:
   a. light source means containing xenon at greater than 3 atmospheres and less than 10 atmospheres pressure, and including a filter assembly to cut off wavelengths below about 300 nanometers;
   b. a housing, adapted to contain said light source means and suitable for handheld operation;
   c. means for pulsing of said light source means; and
   d. light delivery means in operative association with said light source means for delivering radiation within said range from said light source means to the restricted surface area.

2. The apparatus as described in claim 1 wherein said light source means comprises an unconfined arc tube which contains xenon gas maintained at said pressure of 3 to 10 atmospheres.

3. The apparatus as described in claim 2 wherein said xenon pressure is about 4 atmospheres.

4. The apparatus as described in claim 1 wherein said filter assembly has a bandpass characteristic passing wavelengths within the range of about 300 to 500 nanometers.

5. The apparatus as described in claim 1 wherein said filter assembly has a bandpass characteristic passing wavelengths within the range of about 400 to 500 nanometers.

6. The apparatus as described in claim 1 wherein said delivery means comprises flexible optical glass fibers.

7. The apparatus as described in claim 1 wherein said delivery means comprises a liquid-tuned pipe.

8. The apparatus as described in claim 1 wherein said delivery means is a light guide made of rigid quartz.

9. The apparatus as described in claim 1 wherein said delivery means is a light guide made of flexible quartz fibers.

10. Light source apparatus for providing efficient emission of ultraviolet and visible radiation, comprising:
  a. an unconfined xenon arc tube in combination with means for powering and triggering same, said tube providing a substantial continuum of wavelengths over the range of about 300 to 500 nanometers and being maintained at a pressure of at least 3 and less than 10 atmospheres;
  b. a filter assembly for attenuating wavelengths below about 300 nanometers; and
  c. housing means for housing said tube and filter assembly.

11. The apparatus as described in claim 10 comprising a handpiece external of said housing means for delivering light to a restricted area, and transmission means for transmitting light from said tube to said handpiece.

12. The apparatus as described in claim 11 wherein said transmitting means comprises flexible optical fibers.

13. The apparatus as described in claim 11 wherein said transmitting means comprises a light pipe.

14. Light source apparatus for providing efficient emission of radiation within the wavelength range of about 300 nanometers to 500 nanometers, comprising an unconfined arc tube containing a gas maintained at at least about 3 to 4 atmospheres and less than 10 atmospheres, and characterized in that the discharge of said tube provides radiation which is substantially continuous throughout said range, said tube having window means for transmitting therethrough said radiation, which window means cuts off wavelengths below about 300 nanometers, and filter means mounted in registry with said window for optically filtering the radiation transmitted through said window, said filter means including a high cutoff filter for attenuating wavelengths above a predetermined value for wavelengths higher than 500 nanometers.

15. The apparatus as described in claim 14 wherein said filter means comprises a low cutoff filter for further attenuating wavelengths below about 300 nanometers.

16. Light source apparatus for providing efficient emission of radiation within the wavelength range of about 300 nanometers to 500 nanometers, comprising an unconfined arc tube containing a gas maintained at at least about 3 to 4 atmospheres and less than 10 atmospheres, and characterized in that the discharge of said tube provides radiation which is substantially continuous throughout said range, said tube having window means for transmitting therethrough said radiation, which window means cuts off wavelengths below about 300 nanometers, light guide means in registry with said window for guiding the output of said tube along a predetermined guide path, and filter means mounted at about the end of said guide means for optically filtering the radiation transmitted therethrough, said filter means including a high cutoff filter for attenuating wavelengths above about 500 nanometers.

17. The apparatus as described in claim 16 wherein said filter means comprises a low cutoff filter for further attenuating wavelengths below about 300 nanometers.

18. The apparatus as described in claim 16 wherein said light guide means comprises a glass flexible fiber light pipe.

19. The apparatus as described in claim 16 wherein said light guide means comprises a quartz flexible fiber light pipe.

20. The apparatus as described in claim 16 wherein said light guide means comprises a flexible tuned liquid filled light pipe.

21. The apparatus as described in claim 16 wherein said light guide means comprises a rigid quartz light pipe.

22. The apparatus as described in claim 16 wherein said light guide means comprises a flexible plastic light fiber light pipe.

* * * * *